(12) United States Patent
MacKey et al.

(10) Patent No.: US 7,232,930 B2
(45) Date of Patent: Jun. 19, 2007

(54) COMPOUNDS AND METHODS FOR PREPARING METHANESULFONAMIDES

(75) Inventors: Sonja Suzanne MacKey, Galesburg, MI (US); Michael E. Matison, Kalamazoo, MI (US); Haifeng Wu, Portage, MI (US); Michael Paul Goble, San Diego, CA (US); Moses W. McMillan, Portage, MI (US); Vikram Gurudath Kalthod, Mattawan, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 198 days.

(21) Appl. No.: 11/068,287

(22) Filed: Feb. 28, 2005

(65) Prior Publication Data

US 2005/0148796 A1     Jul. 7, 2005

Related U.S. Application Data

(63) Continuation of application No. 10/478,594, filed as application No. PCT/US02/17240 on May 30, 2002, now abandoned.

(60) Provisional application No. 60/327,564, filed on Jun. 5, 2001.

(51) Int. Cl.
    *C07C 303/40*     (2006.01)
    *C07C 311/09*     (2006.01)
    *C07C 211/15*     (2006.01)

(52) U.S. Cl. .................. 564/99; 549/323; 549/475; 560/17; 564/510

(58) Field of Classification Search ................ 549/323, 549/475; 560/12; 564/99, 510
See application file for complete search history.

(56) References Cited

U.S. PATENT DOCUMENTS 5,405,997 A * 4/1995 Hester et al. ................ 564/99

* cited by examiner

*Primary Examiner*—Peter O'Sullivan
(74) *Attorney, Agent, or Firm*—Steven R. Eck; Charles W. Ashbrook

(57) ABSTRACT

A process for preparing (S)-(−)-N-[4-[4-[ethyl(6-fluoro-6-methylheptyl)amino]-1-hydroxy]phenyl]methanesulfonamide hemifumarate salt, which comprises reacting N-[4-[(2S)-tetrahydro-5-hydroxy-2-furanyl]phenyl] methanesulfonamide(IIa) with fluoroamine (III) in the presence of triacetoxyborohydride and ethyl acetate to provide [4-[-4-[ethyl(6-fluoro-6-methylheptyl)amino]-1-hydroxylphenyl]methanesulfonamide (I) and then converting I into the hemifumarate salt Ia. A process for preparing IIa is also claimed as well as intermediates IIa-IId.

12 Claims, No Drawings

COMPOUNDS AND METHODS FOR PREPARING METHANESULFONAMIDES

This application is a continuation of U.S. Ser. No. 10/478 594, filed Nov. 20, 2003, now abandoned, which is a 371 of PCT/US02/17240, filed 30 May 2002, which claims the benefit of 60/327,564, filed 5 Jun. 2001.

BACKGROUND OF THE INVENTION

1. Field of the Invention

This invention relates to a process and compounds useful for the preparation of methanesulfonamides. In particular, it relates to a process and compounds useful for the preparation of (S)-(−)-N[-4[ethyl(6-fluoro-6-methyl-heptyl)amino]-1-hydroxybutyl]phenyl] methanesulfonamide hemifumarate salt. This saltis disclosed in U.S. Pat. No. 5,405,997 as a Class III antiarrhythmic compound which selectively prolongs the action potential duration and concomitantly increases the refractory period of heart cells without significant effects on cardiac condition. The essential parts of U.S. Pat. No. 5,405,997 are herein incorporated by reference.

2. Prior Art

The process described for preparing (S)-(−)-N-[4-[4-ethyl(6-flouro-6-methyl-heptyl) amino-1-hydroxybutyl]phenyl] methanesulfonamide hemifumarate salt in U.S. Pat. No. 5,405,997 involved introduction of the fluoroamine moiety early in the synthesis. This results in the formation of a commercially unacceptable number of impurities.

The use of sodium triacetoxy borohydride for reductive amination of utilizing 1,2-dichloroethane, tetrahydrofuran or acetonitrile as solvents is described in Abdel-Magid, A.F. et al, J. Org. Chem. 1996, 61, 3849-3862.

The direct conversion of a hydroxy ester to a lactone employing basic conditions with no loss in chiral purity was reported by Corey. E.J. et al, J. Am. Chem. Soc. 1987, 109, 7926-7927. However, when subjected to the same basic conditions, hydroxy ester IIc of this invention resulted in a lactone that was racemic.

The use of the enzyme porcine pancreatic lipase to convert hydroxy ester to lactones is also known, Gutman, A. L. et al, J. Org. Chem., 1990, 55, 3546-3552. The conversion of hydroxy acids to lactones under acidic conditions is described by Thompson, A. L. et al, Tetrahedron Lett. 1990, 31, 6953-6956. When the hydroxy ester of this invention is subjected to the ester hydrolysis of Thompson et al, a complex mixture is obtained.

Lactonization of hydroxy esters under acidic conditions has also been reported by Sibi, M. et al, Tetrahedron Let 1992, 5681-5684. Williams et al, Tetrahedron Let, 1989, 1331-1334 and Mohr, P. et al, Helv. Chim. Acta 1987, 142-152.

The complex interaction of physical properties that define the capacity of a compound for upgrading (resolution) was described by Jacques, J. et al, "Enantiomers Racemates and Resolutions", John Wiley & Sons, New York, 1981.

OBJECT OF THE INVENTION

An object of this invention is to provide novel processes and novel compounds for producing (S)-(−)-N-[4-[4-ethyl(6-flouro-6-methyl-heptyl)amino-1-hydroxybutyl]phenyl] methanesulfonamide hemifumarate salt.

Another object of the invention is to provide a process for direct conversion of a hydroxy ester to a lactone without racemization of the chiral center.

Still another object is the utilization of crystallization to upgrade the chiral purity of some of the novel compounds of this invention.

A further object of the invention is to provide a new process for preparing (S)-(−)-N-[4-[-4-[ethyl(6-fluoro-6-methyl-heptyl)amino]-1-hydroxybutyl]phenyl]methanesulfonamide by reductive amination.

SUMMARY OF THE INVENTION

This invention provides a process for producing (S)-(−)-N-[4-[-4-[ethyl(6-fluoro-6-methyl-heptyl)amino]-1-hydroxybutyl]phenyl]methanesulfonamide hemifumarate salt (Ia) which comprises reacting N-[4-[(2S)-tetrahydro-5-hydroxy-2-furanyl]phenyl]methanesulfonamide (IIa) with fluoroamine (III) in the presence of sodium triacetoxy borohydride and ethyl acetate to yield (S)-(−)-N-[4-[-4-[ethyl(6-fluoro-6-methyl-heptyl)amino]-1-hydroxybutyl]phenyl] methanesulfonamide (I) and then converting it to (S)-(−)-N-[4-[-4-[ethyl(6-fluoro-6-methyl-heptyl)amino]-1-hydroxybutyl]phenyl]methanesulfonamide hemifumarate salt.

Further provided is the process defined above, wherein N-[4[(2S)-tetrahydro-5-hydroxy-2-furanyl]phenyl]methanesulfonamide is prepared by (1) subjecting 4-[(methylsulfonyl)amino]-γ-oxobenzenebutanoic acid(IIe) to a Fisher esterification to obtain methyl 4-[(methylsulfonyl)amino]-γ-oxobenzenebutanoate (IId), (2) reducing methyl 4-[(methylsulfonyl)amino]-γ-oxobenzenebutanoate with (−)-DIP-Cl to obtain methyl (γS)-4-[methylsulfonyl)amino]-γ-hydroxybenzenebutanoate (IIc), (3) subjecting methyl (γS)-4-[methylsulfonyl)amino]-γ-hydroxybenzenebutanoate to lactonization with an acid catalyst in the presence of a solvent at a temperature of between −10° to 23° C. to obtain N-[4-[(2S)-tetrahydro-5-oxo-2-furanyl]phenyl]methanesulfonamide (IIb) and (4) reacting N-4-((2S)-tetrahydro-5-oxo-2-furanyl]phenyl]methanesulfonamide with DIBAL-H⁻ in the presence of a solvent and at a temperature of between −35 to −30° C. to obtain N-[4-[(2S)-tetrahydro-5-hydroxy-2-furanyl]phenyl]methanesulfonamide (IIa).

Further provided is a compound having the formula

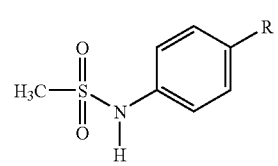

II wherein R is selected from the group consisting of
(a) —C(O)—(CH$_2$)$_2$—C(O)—OCH$_3$
(b) —CH(OH)—(CH$_2$)$_2$—C(O)OCH$_3$
(c) 5-oxo-2-furanyl-
(d) 5-hydroxy-2-furanyl-.

Still further provided is a compound, N-ethyl-6-methyl-6-fluoroheptane amine.

Finally provided is a process for preparing N-ethyl-6-methyl-6-fluoroheptane amine which comprises reacting a solution of 6-bromo-2-fluoro-2-methylheptane with aqueous ethylamine and recovering N-ethyl-6-methyl-6-fluoroheptane amine from the reaction mixture.

DETAILED DESCRIPTION OF THE INVENTION

The present invention provides a process and compounds for preparing (S)-(−)-N-[4-[4-ethyl(6-flouro-6-methyl-heptyl)amino-1-hydroxybutyl]phenyl]methanesulfonamide hemifumarate salt.

Before proceeding further with a description of the preferred embodiments of the present invention, a number of terms will be defined:

"DIBAL-H" means "diisobutylaluminum hydride".
"DIP-Cl" means "(−)-β-chlorodiisopinocampheyl-borane".
"EE" means "enantiomeric excess".
"EtOAc" means "ethyl acetate".
"GC" means "gas chromatography".
"GT" means "greater than".
"LT" means "less than".
"Ms" means "$CH_3SO_2$—".
"MTBE" means "tert-butylmethyl ether".
"NMT" means "not more than".
"RBF" means "round bottom flask".
"THF" means "tetrahydrofuran".

An embodiment of the process of the invention is illustrated in the following schematic representation:

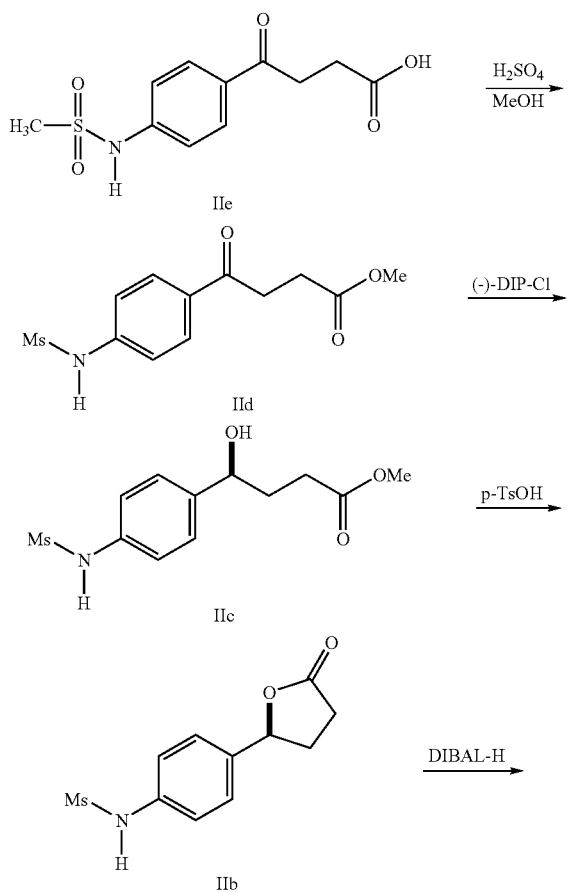

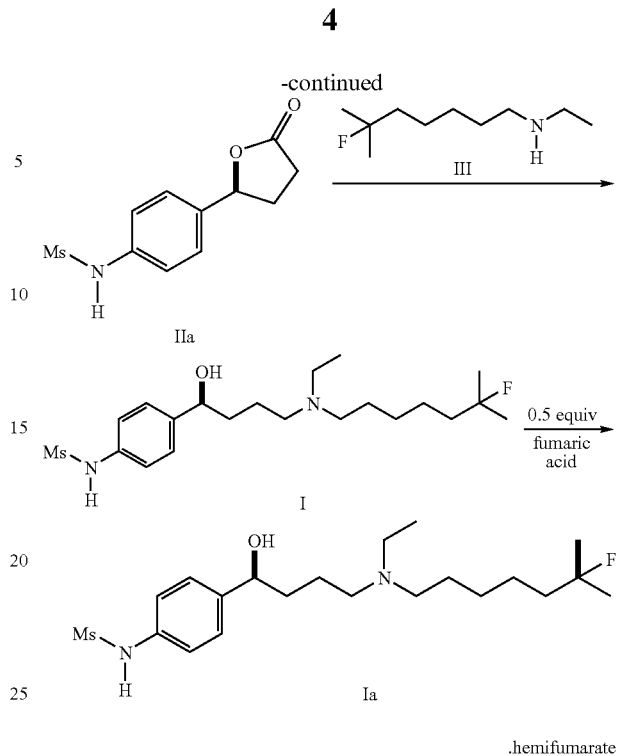

Step 1 involves the Fischer esterification of the compound of Formula IIe to obtain the compound of Formula IId, a suitable compound for asymmetric reduction.

The compound of Formula IIe is either commercially available or can be made by methods well known in the art.

Step 2 involves the installation of the chiral secondary alcohol, which is accomplished by using (−)-DIP-Cl as the asymmetric reductant to give the hydroxy ester of Formula IIc.

In Step 3, the hydroxy ester of Formula IIc is subjected to lactonization in the presence of an acid catalyst and a solvent to yield the lactone of Formula IIb. Acids such as hydrochloric, trichloroacetic, trifluoroacetic, p-toluenesulfonic and acetic acid can be used, but the preferred acids are p-toluenesulfonic, trichloroacetic and trifluoroacetic acids. Temperature is critical in this reaction. The washes must be done cold (0-5° C.) to avoid racemization.

Solvents include ethyl acetate, aceto nitrile, dichloromethane and tetrahydrofuran. Dichloromethane and tetrahydrofuran are preferred.

While the lactonization can be conducted at temperatures of from −10° to 23° C., the higher temperature range leads to erosion or loss of chiral purity. The preferred temperature is 0 to 5° C.

Step 4 involves the reduction of the lactone of Formula IIb with DIBAL-H in the presence of a solvent at a temperature of between −78° to 0° C. to yield lactol IIa. The preferred range is −35° C. to −30° C. Solvents include toluene either alone or with a co-solvent. The preferred solvent is 1:1 methylene chloride/toluene. Over-reduction of the lactone to diol can be minimized by controlling the addition rate of the DIBAL-H between 0.1 and 2.0 ml/min. The preferred rate is 0.5 to 1.0 ml/min. While the reaction ratio will proceed with less than two equivalents per equivalent of lactone, it will be slowed. The preferred stoichiometric ratio is 2.3 equivalents.

Since an excess of DIBAL-H is used, a prequench with ethyl acetate is used to consume the reagent prior to aqueous workup. The amount of ethyl acetate was 1.8 equivalents based on DIBAL-H used. Following the ethyl acetate prequench, the cold reaction mixture was added to a precooled solution of aqueous disodium citrate and then subjected to an extractive work up with ethyl acetate to provide lactol IIa.

The lactol was capable of very efficient chiral upgrading by crystallization from ethyl acetate (1 g/6 mL). Although the most desirable situation was to maintain high chiral purity throughout the entire route, significant upgrading was available if necessary. For example, lactone of 70% ee was converted to lactol having GT 98% ee. The yield was directly related to the level of upgrading required.

Step 5 involves the reductive amination of lactol IIa with fluoroamine III and sodium triacetoxyborohydride in the presence of ethyl acetate. The temperature can range from 0° C. to 25° C. The preferred temperature range is 0 to 5° C. The starting materials for preparing flouroamine III are commercially available or can be made by methods well known in the art.

Fluoroamine III is prepared by reacting a solution comprising 6-bromo-2-fluoro-2-methylheptane in a solvent, such as THF, with aqueous ethylamine and recovering fluoroamine from the reaction mixture.

Step 6 involves reacting the compound of Formula I with fumaric acid in the presence of a solvent in accordance with methods well known in the art for preparing pharmaceutically acceptable salts to yield (S)-(−)-N-[4-[4-[ethyl(6-fluoro-6-methyl-heptyl)amino]-1-hydroxybutyl]phenyl]methanesulfondamide hemifumurate salt Ia.

Preparation 1:

Methyl-4-[(methylsulfonyl)amino]-γ-oxobenzenebutanoate (IId)

4-[(methylsulfonyl)amino]γ-oxobenzenebutanoic acid IIe, (125 g, 0.46 mol) was placed in a flask with 2.5 L of methanol, and 4.6 g of concentrated sulfuric acid (0.047 mol) was added. The slurry was heated to 60° C. for 4 hr, during this period the solids went into solution. After 4 hrs, an aliquot was removed to monitor completion by HPLC. The reaction was determined complete when NMT 2% of the starting material remained. The solution was cooled to 21° C., allowing the product to crystallize. The slurry was cooled to 0° C., and the product was collected by filtration. The filter cake was washed with a mixture of 375 ml of methanol and 12.5 ml of triethylamine (×2), followed by 375 mL of methanol. The title product was obtained in 92% yield (99 area %). Melting point 181-183° C. $^1$H NMR (400 MHz, DMSO-$d_6$) δ 10.32 (s, 1H), 7.95 (d, J=8.4 Hz, 2H), 7.30 (d, J=8.8 Hz, 2H), 3.58 (s, 3H), 3.2(s, 1H), 3.24 (t, J=6.4 Hz, 2H), 3.1 (s, 3H), 2.63 (t, J=6.4 Hz, 2H); $^{13}$C NMR (100 MHz, DMSO-$d_6$) δ C 196.8, 172.8, 143.0, 131.0; CH 129.6, 117.5; $CH_2$ 32.7, 27.6; $CH_3$ 51.3, 39.8; MS m/z calcd for $C_{12}H_{14}NO_5S$ 284.31 $(M-H)^+$; found 284.00 $(M-H)^+$.

Preparation 2:

Methyl(γS)-4-[(methylsulfonyl)amino]-γ-hydroxy-benzenebutanoate (IIc)

Methyl 4-[(methylsulfonyl)amino]-γ-oxobenzene-butanoate from Preparation 1 was placed into a 1 L flask fitted with mechanical stirring and temperature probe. Tetrahydrofuran (2000 ml) was added to form a slurry. In a nitrogen box, (−)-DIP-Cl (362.6 g, 1.130 mol, 2.15 equiv) was weighed into an addition funnel and dissolved in 500 ml of tetrahydrofuran. The addition funnel was fitted to the flask and the system was flushed with nitrogen. The slurry in the flask was cooled to 0° C.; and the DIP-Cl solution was added dropwise. There was very little exotherm. The addition can go fast as long as pot temp. was kept at about 0° C. The reaction was stirred for 72-96 hours at 0° C. Monitored by HPLC (conditions below) for completion (LT 1% methyl ester). The slurry turned into a clear, colorless solution as the reaction progressed.

When the reaction was determined complete, acetone was added (200 ml, 6 equiv) to quench the reaction. The mixture was stirred at 0° C. for an hour, then it was warmed to 23° C. The mixture was washed with a 50% aqueous solution of $NaHCO_3$ (3×1000 ml). (Note: Significant formation of $CO_2$ gas!) The combined aqueous phase was extracted with MTBE (2×1000 ml). The organics were combined and washed with 1000 ml brine. The solution was concentrated under reduced pressure, then swapped to MeOH under reduced pressure to a final volume of 1500 ml. This MeOH solution was washed with heptanes (4×1000 ml). The MeOH solution was then concentrated under reduced pressure and swapped to $CH_2Cl_2$ for a final volume of less than 1000 ml. Washed the solution with 1000 ml brine and dried through a plug of $MgSO_4$. This solution was cooled (−15° C.) to promote crystallization. (Note: A slight vacuum may be applied if necessary, but only until solids begin to crystallize.) Hold the resulting slurry at −15° C. for 3-4 hours. The product was collected by filtration, using heptanes to rinse flask and wash cake, and dried on nitrogen press. The title product was obtained as white, powdery solid (132.5 g, 88% yield). Melting point 70-72° C. $^1$H NMR (400 MHz, $CDCl_3$) δ 7.09 (d, J=8.4 Hz, 2H), 6.96 (dd, J=4.9, 8.4 Hz, 2H), 4.51 (dd, J=6.3, 6.4 Hz, 1H), 3.45 (s, 3H), 2.77 (s, 3H), 2.21 (t, J=7.2 Hz, 2H), 1.81 (dt, J=6.8, 6.8 Hz, 2H); $^{13}$C NMR (100 MHz, $CDCl_3$) δ C 174.4, 141.2, 136.1; CH 127.1, 120.9, 72.8; $CH_2$ 33.7, 30.3; $CH_3$ 51.8, 39.2; MS m/z calcd for $C_{13}H_{19}NO_5S$, 286.075 $(M-H)^+$; found 285.94 $(M-H)^+$.

Preparation 3:

N-[4-[(2S)-Tetrahydro-5-oxo-2-furanyl]-phenyl]methanesulfonamide (IIb)

Methyl (γS)-4-[(methylsulfonyl) amino]-γ-hydroxybenzenebutanoate (17.9 g, 62.3 mmol) from Preparation 2 was placed in a flask with 350 ml of $CH_2Cl_2$ and the resulting slurry was cooled to 0° C. To this mixture was added 0.12 g of p-TsOH•$H_2O$ (1.5 mol %). The reaction was monitored for completion by HPLC until NMT 2% hydroxy ester remained (expect 4-6 h). The reaction mixture was washed with $H_2O$ (2×250 ml) and brine (250 ml) while maintaining the temperature at 0° C. The pH of the final wash must be maintained at GT 5). The organic layer was dried with $MgSO_4$, filtered and concentrated under reduced pressure. The resulting solids were recrystallized from EtOAc (25 ml) to provide 12.1 g (76% yield) of the title compound as white solids (95 area %, 97% ee). Melting point 101-102° C. $^1$H NMR (400 MHz, $CDCl_3$) δ 7.24 (dt, J=8.0, 8.6 Hz, 4H), 5.43 (m, 1H), 2.97 (s, 3H), 2.63 (m, 3H), 2.14 (m, 1H); $^{13}$C NMR (100 MHz, $CDCl_3$) δ C 177.0, 137.2, 136.0; CH 126.8, 120.7, 80.9; $CH_2$ 30.7, 29.0; $CH_3$ 39.4; MS m/z calcd for $C_{11}H_{13}NO_4S$, 255.056 $(M^+)$; found 254.95 $(M^+)$.

Preparation 4:

N-[4-[(2S)-Tetrahydro-5-hydroxy-2-furanyl]phenyl]methanesulfonamide (IIa)

N-[4-[(2S)-Tetrahydro-5-oxo-2-furanyl]-phenyl]methanesulfonamide (IIb) from Preparation 3 (9.823 g, 38.5 mmol) was dissolved in a $CH_2Cl_2$/toluene (100 ml/41 ml) at 23° C., then cooled to −30° C. The mixture was a slurry. DIBAL-H (59 ml, 1.5 M in toluene) was added slowly to the mixture (1 ml/min). After addition was complete, the solution was stirred until less than 1% of lactone remained by HPLC assay. When the reaction was complete, excess DIBAL-H was pre-quenched with EtOAc (15 ml). This mixture was then added to a pre-cooled (0° C.) aqueous solution of disodium citrate (1.0 M, 200 ml). The reaction mixture was not allowed to warm during this addition period. Ethyl acetate (200 ml) was added, and the resulting two-phase mixture was stirred for at least 5 hours. The organic layer was separated, and the aqueous layer was extracted with EtOAc (2×100 ml). The combined organic layers were washed with brine (2×150 ml). The solvent was removed under reduced pressure. The crude solids were crystallized from ethyl acetate (6 mL/g). A white solid was obtained (8.04 g), having 3% diol by area. Recrystallization from ethyl acetate provided 6.4 g of the title product as a white, powdery solid (64% yield, 93 area %, GT 99% ee). Melting point=129-130° C. $^1$H NMR (400 MHz, CD$_3$OD) δ 7.42 (d, J=8.2 Hz, 1H), 7.29 (d, J=8.2 Hz, 1H), 7.29 (d, J=8 Hz, 1H), 7.21 (d, J=8.1 Hz, 2H), 5.65 (m, 0.5H), 5.53 (m, 0.5H), 5.14 (t, J=6.9 Hz, 0.5H), 4.93 (t, J=7.6 Hz, 0.5H), 2.92 (s, 3H), 2.49 (m, 1H), 2.25 (m, 1H), 1.98 (m, 1H), 1.92 (m, 1H); $^{13}$C NMR (100 MHz, CD$_3$OD) δ C 142.9, 141.2, 140.6, 138.6, 138.5; CH 128.4, 127.9, 121.7, 121.6, 99.9, 99.5, 83.2, 80.3, 74.4, 74.3; CH$_2$ 35.5, 35.1, 34.4, 34.2, 33.9; CH$_3$ 39.1, 39.0. MS (EI) m/z calcd for C$_{11}$H$_{15}$NO$_4$S 257.07 (M$^+$).

Preparation 5:

7-bromo-2-hydroxyl-2-methylheptane

A first reaction vessel was charged with ethyl 6-bromohexanoate (175 g) and the line was rinsed with 177 g of THF. The solution cooled to −20° C. A second reaction vessel was charged with 2-M methyl magnesium chloride in THF (902 g). The solution was cooled to −20° C. The 6-bromohexanoate solution was transferred to the second reaction vessel keeping the temperature in the second reaction vessel less than 10° C. The first reaction vessel was rinsed with 50 g of THF. The reaction was assayed by GC (15 m DB-1 0.25 micron ID column. 70° C. for 5 minutes to 275° C. at 20° C./min with injector at 140° C. and detector at 250° C.) until less than 2% of starting material remained.

Water (580 ml) was charged to the first reaction vessel followed by concentrated HCl (192 g). The solution was cooled to 10-15° C. The reaction mixture was transferred to the acid solution keeping the temperature less than 20° C. Toluene (920 ml) was added and the phases were separated. The aqueous phase was back extracted with toluene (200 ml) and discarded. The combined organic phases were washed with saturated sodium chloride (700 ml). The 7-bromo-2-hydroxyl-2-methylheptane could be isolated by distillation of the solvent under reduced pressure.

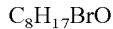
$^1$H NMR (400 MHz, CDCl$_3$) δ 3.38 (t, J=7.8 Hz, 2H), 1.78 (m, 2H), 1.58 (m, 2H), 1.3 (m, 4H), 1.20 (s, 6H); $^{13}$C NMR (100 MHz, CDCl$_3$) δ 70.9, 42.8, 33.7, 33.2, 29.5, 27.9, 22.8.

Preparation 6:

6-bromo-2-fluoro-2-methylheptane 500 ml of branched octanes (commercially available) and anhydrous HF (110 g) were charged to a reaction vessel and the mixture cooled to −20 to −30° C. A solution of 7-bromo-2-hydroxyl-2-methylheptane (281 g) in branched octanes (1000 ml) was added to the HF and stirred at −20 to −30° C. for 7 hours. A sample was tested at 20° C./min with injector at 140° C. and detector at 250° C.) and showed less than 0.5% of the starting alcohol. The reaction was quenched by addition in a solution of potassium carbonate (1906 g) in water (1800 ml). The phases were separated and the organic distilled to a volume of 500 ml. The 6-bromo-2-fluoro-2-methylheptane could be isolated by vacuum distillation or carried directly into the next reaction.

$^1$H NMR (400 MHz, CDCl$_3$) δ 3.38 (t, J=16 Hz, 2H), 1.78 (m, 2H), 1.59 (d of t, J=24 Hz J=8 Hz, 2H), 1.48 (m, 2H), 1.35 (d, J=24 Hz, 6H); $^{13}$C NMR (100 MHz, CDCl$_3$) δ 99.6 (d, J=45 Hz), 41.1 (d, J=16 Hz), 33.7, 33.2, 27.9, 27.1, 22.5. MS (ESI+) for C$_8$H$_{16}$BrF m/z 212 (M+H)$^+$. Anal Calcd for C$_8$H$_{16}$BrF: C, 45.51; H, 7.64; F, 9.0; Br, 37.85; found: C, 45.65; H, 7.76; F, 8.94.

Preparation 7:

N-ethyl-6-methyl-6-fluoroheptane amine

The 6-bromo-2-fluoro-2-methylheptane solution prepared in Preparation 6 (283 g) was charged to a reaction vessel. The solution was concentrated to 450 ml by vacuum distillation and THF (765 g) was added followed by 70% aqueous ethylamine (557 g). The reaction was stirred at 30-35° C. for 6 hours. The reaction was cooled and water (900 ml) and methylene chloride (900 ml) were added. The phases were separated and the aqueous back washed with methylene chloride (900 ml). The combined organic layers were washed with water (450 ml) and concentrated to a volume of 450 ml by vacuum distillation. THF (810 g) was added and the solution concentrated to a volume of 450 ml. This solvent displacement was repeated and the N-ethyl-6-methyl-6-fluoroheptane amine packaged as a THF solution.

$^1$H NMR (400 MHz, CDCl$_3$) δ 2.66 (t, J=4 Hz, 2H), 2.61 (q, J=8 Hz, 2H), 1.48 (m, 2H), 1.42 (m, 2H), 1.38 (m, 2H), 1.34 (d, J=24 Hz, 6H), 1.15 (t, J=8 Hz, 3H); $^{13}$C NMR (100 MHz, CDCl$_3$) δ 99.6 (d, J=43 Hz), 49.0, 44.4, 41.6 (d, J=23 Hz), 28.13, 27.9, 27.1, 21.9, 15.52. Anal Calcd for C$_{10}$H$_{22}$FN: C, 68.52; H, 12.65; F, 10.84; N, 7.99; found: C, 68.65; H, 12.66; F, 10.89, N, 7.80.

EXAMPLE 1

(S)-(−)-N-[4-[-4-[ethyl(6-fluoro-6-methyl-heptyl) amino]-1-hydroxybutyl]phenyl]methanesulfonamide (I)

N-[4-[(2S)-Tetrahydro-5-hydroxy-2-furanyl]phenyl] methanesulfonamide (10.0 g, 38.9 mmol) from Preparation 4 and N-ethyl-6-methyl-6-fluoroheptane amine (99% pure, 6.8 g, 38.9 mmol) from Preparation 7 were stirred with EtOAC (25 ml) in a flask for 1 hour. The slurry became clear solution, indicating formation of the iminium salt. Sodium triacetoxyborohydride (11.5 g, 54.4 mmol) was placed in a separate flask with EtOAc (50 ml). The mixture was cooled to 0° C. The first solution (iminium salt) was added slowly to the second mixture with vigorous stirring. The temperature was maintained at 0 to 4° C. After the addition was complete, the flask was rinsed with EtOAc (10 ml), and that was added also. The mixture was stirred overnight at 0° C. Water (100 ml) was added to quench the excess reagent, while the temperature was maintained at 0 to 4° C. While cooling was maintained, the pH was raised to 6.5 using a 10% aqueous sodium hydroxide solution. The layers were separated, and the aqueous was extracted with EtOAc (2×50 ml). The aqueous layer was then adjusted to pH 8.2, and the product was extracted with EtOAc (3×100 ml). The solvent was removed under reduced pressure to provide the title product as a colorless oil (14.9 g) in 92% yield. TLC 100% EtOAc, Rf=0.15.

EXAMPLE 2

(S)-(–)-N-[4-[-4-[ethyl(6-fluoro-6-methyl-heptyl) amino]-1-hydroxybutyl]phenyl]methanesulfonamide hemifumarate Salt (Ia)

A 50 ml portion of (S)-(–)-N-[4-[-4-[ethyl(6-fluoro-6-methyl-heptyl)amino]-1-hydroxybutyl]phenyl]methanesulfonamide, from Example 1, ethyl acetate solution (contains 7.78 g 18.7 mmol) was placed into a 100 ml RBF. The solvent was removed under reduced pressure. Tetrahydrofuran (40 ml) was added, and the solvent was removed under reduced pressure. Another 40 ml of THF was added, and the solution was concentrated to a volume of 15 ml. A 250 ml 4-neck RBF was charged with fumaric acid (1.08 g, 9.34 mmol) and 80 ml of THF. This mixture was heated to 40 to 45° C., and the solids went into solution. The THF solution of (S)-(–)-N-[4-[-4-[ethyl(6-fluoro-6-methyl-heptyl) amino]-1-hydroxybutyl]phenyl]methanesulfonamide was added to the fumaric acid solution, rinsing with 20 ml of THF. The mixture was stirred at 40 to 45° C. for 30 min., then concentrated to 45 ml under vacuum. The mixture was then heated to reflux (bath temp 75 to 80° C.) for 30 min., then cooled to 45 to 50° C. over a 30 min. period. To this was added 0.05 g of (S)-(–)-N-[4-[-4-[ethyl(6-fluoro-6-methyl-heptyl)amino]-1-hydroxybutyl]phenyl]methanesulfonamide hemifumarate salt (Ia) seed crystals. The mixture was stirred at 45 to 50° C. for 15 min.

Using a syringe pump (0.6 ml/h), 14 ml of branched octane was added while maintaining the pot temperature at 45 to 50° C. The mixture formed an oil rather than the expected solids, so another portion of PNU-108342E seed crystals was added. The mixture was stirred at 45 to 50° C. for 24 hours, and the mixture formed a thick slurry during this time. A 60 ml coarse fritted filter was preheated to 45 to 50° C., and used to collect the solids. The cake was washed in two parts using a mixture of 20 ml of THF and 5 ml of branched octane; then the cake was washed in two parts using 25 ml of branched octane. The cake was dried in the vacuum oven at 40 to 45° C. The title compound was obtained as a hard cake of white solids (8.1 g, 17.3 mmol, 92%).

What is claimed is:

1. A process for preparing (S)-(–)-N-[4-[-4-[ethyl(6-fluoro-6-methyl-heptyl)amino]-1-hydroxybutyl]phenyl] methanesulfonamide (I) which comprises reacting N-[4 [(2S)-tetrahydro-5-hydroxy-2-furanyl]phenyl] methanesulfonamide (IIa) with flouroamine (III) in the presence of triacetoxy borohydride and ethyl acetate.

2. A process according to claim 1, wherein N-[4[(2S)-tetrahydro-5-hydroxy-2-furanyl]phenyl]methanesulfonamide is prepared by (1) subjecting 4-[(methylsulfonyl) amino]-γ-oxobenzenebutanoic acid(IIe) to a Fisher esterification to obtain methyl 4-[(methylsulfonyl)amino]-γ-oxobenzenebutanoate (IId), (2) reducing methyl 4-[(methylsulfonyl)amino]-γ-oxobenzenebutanoate with (–)-DIP-Cl to obtain methyl (γS)-4-[methylsulfonyl)amino]-γ-hydroxybenzenebutanoate (IIc), (3) subjecting methyl(γS)-4-[methylsulfonyl)amino]-γ-hydroxybenzenebutanoate to lactonization with an acid catalyst in the presence of a solvent at a temperature of between –10° to 23° C. to obtain N-[4-[(2S)-tetrahydro-5-oxo-2-furanyl]phenyl]methanesulfonamide (IIb) and reacting N-[4-[(2S)-Tetrahydro-5-oxo-2-furanyl] phenyl]methanesulfonamide with DIBAL-H in the presence of a solvent and at a temperature of between –35 to –30 C obtain N-[4-[(2S)-tetrahydro-5-hydroxy-2-furanyl]phenyl] methanesulfonamide.

3. A process according to claim 1, wherein (S)-(–)-N-[4-[-4-[ethyl(6-fluoro-6-methyl-heptyl)amino]-1-hydroxybutyl]phenyl]methanesulfonamide is further reacted with fumaric acid to obtain (S)-(–)-N-[4-[-4-[ethyl(6-fluoro-6-methyl-heptyl)amino]-1-hydroxybutyl]phenyl]methanesulfonamide hemifumarate salt.

4. A compound having the formula

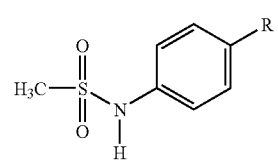

II wherein R is selected from the group consisting of
(a) —C(O)—(CH$_2$)$_2$—C(O)OCH$_3$
(b) —C(OH)—(CH$_2$)$_2$—C(O)OCH$_3$
(c) 5-oxo-2-furanyl-
(d) 5-hydroxy-furanyl-.

5. A compound according to claim 4, wherein R is selected from the group consisting of —C(O)—(CH$_2$)$_2$—C(O)OCH$_3$ and —CH(OH)—(CH$_2$)$_2$—C(O)OCH$_3$.

6. A compound according to claim 5, methyl 4-[(methylsulfonyl)amino]-γ-oxobenzenebutanoate.

7. A compound according to claim 5, methyl (γS)-4-[methylsulfonyl)amino]-γ-hydroxybenzene-butanoate.

8. A compound according to claim 4, wherein R is selected from the group consisting of 5-oxo-2-furanyl- and 5-hydroxy-furanyl.

9. A compound according to claim 8, N-[4-[(2S)tetrahydro-5-oxo-2-furanyl]phenyl]methane-sulfonamide.

10. A compound according to claim 8, N-[4-[(2S)-tetrahydro-5-hydroxy-2-furanyl]phenyl]methane-sulfonamide.

11. A fluoroamine compound, N-ethyl-6-methyl-6-fluoroheptane amine.

12. A process for preparing N-ethyl-6-methyl-6-fluoroheptane amine which comprises reacting a solution of 6-bromo-2-fluoro-2-methylheptane with aqueous ethylamine in the presence of a solvent and recovering the N-ethyl-6-methyl-6-fluoroheptane amine from the reaction mixture.

* * * * *